(12) United States Patent
Bielawski (10) Patent No.: US 8,379,201 B2
(45) Date of Patent: Feb. 19, 2013

(54) METHOD AND DEVICES FOR IMAGING A SAMPLE

(75) Inventor: Jacek Bielawski, Uppsala (SE)

(73) Assignee: GE Healthcare Bio-Sciences AB, Uppsala (SE)

(*) Notice: Subject to any disclaimer, the term of this patent is extended or adjusted under 35 U.S.C. 154(b) by 1370 days.

(21) Appl. No.: 11/913,850

(22) PCT Filed: May 8, 2006

(86) PCT No.: PCT/EP2006/004274
§ 371 (c)(1),
(2), (4) Date: Nov. 21, 2007

(87) PCT Pub. No.: WO2006/119941
PCT Pub. Date: Nov. 16, 2006

(65) Prior Publication Data
US 2009/0127115 A1    May 21, 2009

(30) Foreign Application Priority Data
May 11, 2005 (GB) .................... 0509611.0

(51) Int. Cl.
*G01J 3/30* (2006.01)
(52) U.S. Cl. ........................ 356/317; 356/244
(58) Field of Classification Search ........ 356/317, 356/244; 422/563
See application file for complete search history.

(56) References Cited

U.S. PATENT DOCUMENTS

| | | | |
|---|---|---|---|
| 3,861,781 A | 1/1975 | Hasegawa et al. | |
| 4,037,109 A * | 7/1977 | Hosokawa et al. | 378/45 |
| 4,040,747 A * | 8/1977 | Webster | 356/418 |
| 4,974,952 A * | 12/1990 | Focht | 359/398 |
| 6,027,628 A * | 2/2000 | Yamamura et al. | 204/618 |
| 6,037,168 A * | 3/2000 | Brown | 435/305.2 |
| 6,043,880 A * | 3/2000 | Andrews et al. | 356/417 |
| 6,159,425 A | 12/2000 | Edwards et al. | |
| 6,163,590 A * | 12/2000 | Wilkins | 378/43 |
| 6,379,516 B1 | 4/2002 | Cabilly et al. | |
| 6,841,132 B2 * | 1/2005 | Samsoondar | 422/560 |
| 2004/0071394 A1 | 4/2004 | Gfrorer et al. | |
| 2005/0008541 A1 | 1/2005 | Hochstrasser et al. | |

FOREIGN PATENT DOCUMENTS

| | | |
|---|---|---|
| GB | 2294320 | 4/1996 |
| WO | WO 96/34276 | 10/1996 |
| WO | WO99/42608 | 8/1999 |
| WO | WO02/077630 | 10/2002 |
| WO | WO2004/074818 | 9/2004 |

OTHER PUBLICATIONS

Tonge, R., Shaw, J., Middleton, B., Rowlinson, R., Rayner, S., Young, J., Pognan, F., Hawkins, E., Currie, I. & Davison, M. (2001). "Validation and development of fluorescence two-dimensional differential gel electrophoresis proteomics technology". Proteomics, 1(3) 377-396.

Ünlü, M., Morgan, M. E. & Minden, J. S. (1997). "Difference gel electrophoresis: A single gel method for detecting changes in protein extracts". Electrophoresis, 18(11) 2071-2077.

* cited by examiner

*Primary Examiner* — Kara E Geisel (57) ABSTRACT

The invention relates to methods and devices for imaging a sample, in particular to methods and devices for imaging electrophoretic gels which have been used to separate biological molecules such as proteins or nucleic acids. The invention overcomes the problems associated with interference due to Newton's Rings and chemical toxicity experienced with conventional imaging systems.

12 Claims, 6 Drawing Sheets

Fig. 6d

METHOD AND DEVICES FOR IMAGING A SAMPLE

CROSS-REFERENCE TO RELATED APPLICATIONS

This application is a filing under 35 U.S.C. §371 and claims priority to international patent application number PCT/EP2006/004274 filed May 8, 2006, published on Nov. 16, 2006, as WO 2006/119941, which claims priority to patent application number 0509611.0 filed May 11, 2005 in Great Britain; the disclosures of which are incorporated herein by reference in their entireties.

TECHNICAL FIELD

The present invention relates to methods and devices for imaging a sample, in particular methods and devices for imaging electrophoretic gels which have been used to separate biological molecules such as proteins or nucleic acids.

BACKGROUND OF THE INVENTION

The imaging of samples to provide identification and/or quantification of an analyte present within the sample is an important process in many branches of chemical and biological research. Analytes may be identified and quantified directly within a sample by measuring, for example, chemiluminescence or radioactivity; alternatively, the analyte may first require derivatisation with a detectable label, such as a fluorescent dye, prior to image analysis. Imaging devices consequently use a variety of detectors to identify and quantify such analytes, ranging from photodiodes, photomultiplier tubes (PMT) to charge coupled device (CCD) cameras. A variety of imaging devices are commercially available depending upon the desired modality (e.g. fluorescence, phosphorescence, storage phosphor imaging, chemiluminescence). These imaging devices are designed to image samples which have a variety of different formats such as microtitre or microwell plates, slides, membranes, tissue slices or sections, cuvettes, tubes, gels or cassettes.

US 2004/0071394, for example, describes an imaging system with a sample holder which is designed to hold multiple slides and has the dimensions of a microplate. GB2294320 concerns an imaging device used for studying bacterial colonies which are sealed within a gel cassette system. In this example, a laser beam is passed through the cassette to generate light scattering data which can be analysed to determine bacterial growth. Yet other imaging devices are disclosed in U.S. Pat. No. 6,159,425, together with support devices for sample containers which are to be imaged. The support devices comprise a holder which supports but does not enclose the sample container on a shelf structure.

The imaging of biological molecules such as nucleic acids and proteins is of particular importance in biological research. There is a continuing need to identify and quantify proteins and nucleic acids originating from a diverse range of organisms spanning simple bacteria to biologically complex mammals. Following the success of the human genome project in which the genetic sequence of the genome was determined, there is growing scientific interest in characterising the protein composition and protein function in man and other organisms.

The separation of biological molecules, such as proteins and nucleic acids, prior to or in parallel with their identification and quantification, can be achieved by a variety of techniques. Gel electrophoresis is a technique used to determine the size and subunit composition of proteins. An electric field is applied to a solution containing a protein and, because it is a charged molecule, the protein then migrates through a gel at a rate that depends on its net charge, size, and shape. The gel is then fluorescently stained to reveal the different protein components. The gel is imaged using a fluorescence imaging device to allow identification and quantification of the individual proteins. Two-dimensional gel electrophoresis is an advanced technique that can resolve with great accuracy more than 1000 different proteins and provide a virtual 'map' of all the proteins present in a solution.

Proteomic analysis utilising 2-D polyacrylamide gel electrophoresis (PAGE) protein separation is another technique which is widely used but is relatively low-throughput due to the time-consuming process of image analysis which is required to determine differential protein expression. A more efficient process, known as 2-D Difference Gel Electrophoresis, utilises fluorescent dyes to label proteins prior to 2-D PAGE, allowing multiple samples to be co-separated and visualised on one gel. Typically, three protein extracts (e.g. one control and two treated) are labelled with different fluorescent dyes (e.g. Cy2, Cy3 and/or Cy5) then combined and separated by 2-D PAGE. Images are then captured using the Cy2, Cy3 and/or Cy5 excitation wavelengths and the difference between the samples determined by image analysis software to allow identification and quantification of the protein components in each sample (Unlu et al., 1997, *Electrophoresis*, 18, 2071-77; Tonge et al., 2001, *Proteomics*, 1,377-396).

However, the scanning of gels which have been used for electrophoretic separation of biological molecules with conventional scanners is fraught with technical difficulties. Thus, for instance, the gels are typically laid out upon the glass window or platform of an imaging device such as a fluorescence scanner and the lid of the scanner closed prior to scanning. After the imaging process has been completed, which is generally some 30 minutes later, the gels must be carefully removed (if they are to be retained) and the window or platform washed thoroughly. As this cleaning process often involves the use of corrosive solvents and chemicals, considerable care must be taken to avoid user injury and/or damage to the imaging device. In order to ensure that the interior of the device is protected from these chemicals and solvents, the glass window or platform must be sealed to prevent access of the corrosive cleaning materials to vulnerable components within the body of the machine. Alternatively, the components of the imaging device must be constructed of materials which are known to tolerate the cleaning chemicals and solvents.

The use of corrosive chemicals and solvents within an instrument lab, as opposed to a fume hood, raises additional difficulties for the user. In some instances, the instrument may need to be housed within a fume hood which is wasteful of this expensive resource.

Another problem experienced with imaging systems of the prior art is that of 'Newton's Rings', an interference phenomenon caused by light passing through two sheets of glass. Newton's Rings are concentric rings which appear when two sheets of glass or clear plastic are held close together and almost in parallel to each other. The rings appear when the air gap between the sheets is of a certain size relative to the wavelength so that the light rays encounter interference.

Such phenomena generally occur when a sample, contained within a glass or a plastic retainer, is imaged directly on the glass platform of an imaging device, the light thus having to pass through several glass sheets. This can happen when, for example, a sample contained within a glass or plastic container/slide is placed on the glass platform of the imaging device. The problem may also arise if a gel is sandwiched between two glass sheets forming a cassette and this cassette is positioned on top of the glass platform of an imaging device. Cassettes of this nature are commonly used within the industry and are commercially available (e.g. The Gel Company, San Francisco, Calif., USA) to save operator time, improve gel uniformity and facilitate handling and storage. The net result is an inaccurate intensity reading due to the non-uniformity caused by the Newton's Rings formed by interaction between the glass platform of the imaging device and the glass sheet of the cassette.

Existing cassettes, of the type described above, can have limited use in terms of storage of a sample. Thus, for instance, gels may desiccate with time because the cassette is not sealed to the environment. Furthermore, contamination of the sample or gel can occur if efforts are not made to protect or seal it from its environment.

US 2005/0008541 describes a gel holder which can be used in a method for locating gel pieces using a scanner and removing the located pieces from the gel. The base plate of the holder is transparent to electromagnetic radiation in order to allow optical scanning or detection of concentration points in the gel. However, the gel holder does not comprise any locking device to seal the gel and thus prevent desiccation and contamination from the environment.

Caddies or structures for housing and holding multi-well platforms in a planar configuration to facilitate optical reading are disclosed in WO 1999/042608. The caddies can be adapted for robotic handling or optical reading and may be fitted with lids. However, no releasable locking devices are used to seal the caddies from the environment.

WO 2004/074818 describes a case for a microfluidic sample array which comprises a frame, top and bottom which, in operation, are sealed together to be tight to liquids. At least one of the top or bottom structures are light transmissive to facilitate optical reading. The case lacks any locking device which can be used to protect any sample enclosed within it, the component parts simply being sealed together, if required, after the sample is inserted within it.

The present invention seeks to address the aforementioned problems with the prior art and to provide solutions thereto, principally in the form of a method for imaging a sample, an imaging device and a frame for the device.

SUMMARY OF THE INVENTION

According to a first aspect of the invention, there is provided a method for imaging a sample comprising the following steps:
(i) enclosing the sample in a frame, the frame comprising a first portion and a second portion, wherein the first portion comprises a window which is transparent to imaging electromagnetic radiation;
(ii) positioning the frame in an imaging device, the imaging device comprising an electromagnetic radiation detector and a platform having a pane free opening for supporting the frame, with the window facing the detector and the opening between the window and the detector; and
(iii) capturing electromagnetic radiation emanating from the sample with the detector Suitably, step (i) provides an hermetic seal between the first portion and the second portion.

Suitably, the method additionally comprises the step of irradiating the sample with electromagnetic radiation following step (ii).

Suitably, the irradiating radiation is scanned across the sample.

Preferably, the imaging device is selected from the group consisting of fluorescence/phosphorescence imager, storage phosphor imager and chemiluminescence imager.

Preferably, the detector is a photomultiplier tube (PMT). More preferably, the detector is a fluorescence detector. Most preferably, the detector is a charge coupled device (CCD).

Suitably, the window lacks a pane.

Alternatively, the window comprises a low fluorescence plastic or glass pane.

Preferably, the detector is a scanning fluorescence detector.

Suitably, the sample is enclosed within a container and the container is enclosed within the frame. The container may, for example, be a dish or a bag made of a material which is transparent to imaging electromagnetic radiation.

Suitably, the sample is held within a cassette and the cassette is enclosed within the frame. The cassette may, for instance, comprise two glass or plastic sheets. These sheets can enclose the sample, forming a sandwich with the sample enclosed between them. On enclosing the sample, the sheets may be fused together to form a sealed unit to protect the sample.

Suitably, the sample is suitable for Differential Interference Gel Electrophoresis (DIGE) analysis.

Suitably, the frame and the detector are movable relative to each other in order to allow capture of electromagnetic radiation and/or scanning of the sample surface. This may be achieved by means of a staging mechanism in the imaging device.

Suitably, the sample is selected from the group consisting of gel, membrane, tissue slice or section, liquid, microtitre plate, cuvette, tube, microscope slide and cassette.

According to a second aspect of the present invention, there is provided an imaging device for imaging a sample enclosed within a frame wherein the first portion comprises a body delimiting a window which is transparent to imaging electromagnetic radiation and the second portion is in the form of a lid which is opaque to imaging electromagnetic radiation, characterised in that the device comprises a platform which has a pane free opening for supporting the frame.

Preferably, the imaging device additionally comprises a staging mechanism for movement of the frame to enable scanning of the sample.

Suitably, the device of the second aspect is selected from the group consisting of storage phosphor imager, chemiluminescence scanner, fluorescence scanner/phosphorescence scanner. Preferably, the device is a fluorescence scanner.

Suitably, the sample is selected from the group consisting of gel, membrane, tissue slice or section, liquid, microtitre plate, microscope slide and cassette for a gel.

According to a third aspect of the present invention, there is provided a frame for an imaging device for enclosing a sample within, the frame comprising a first portion and a second portion and a releasable locking device for sealing the first portion to the second portion, characterised in that the first portion comprises a body delimiting a window which is transparent to imaging electromagnetic radiation and a second portion in the form of a lid which is opaque to imaging electromagnetic radiation.

Suitably, the window lacks a pane.

Preferably, the window comprises a low fluorescence glass or plastic pane. More preferably, the glass or plastic pane is attached to the first portion by a seal to prevent leakage of liquid from the frame. Most preferably, the pane comprises a series of reference points printed on its surface to facilitate positioning and the determination of X and Y co-ordinates during image analysis.

Suitably, the first portion comprises spring-loaded retainers for securing the sample thereto.

Preferably, the first portion and/or the second portion comprises a low fluorescence material or is coated with a low fluorescence material.

Suitably, the first portion comprises at least one handle to facilitate carriage of the frame.

Suitably, the sample is selected from the group consisting of gel, membrane, tissue slice or section, liquid, microtitre plate, microscope slide and cassette for a gel.

In a fourth aspect of the present invention, there is provided a system for imaging a sample comprising
i) a frame for an imaging device as hereinbefore described; and
ii) an imaging device as hereinbefore described.

BRIEF DESCRIPTION OF THE DRAWINGS

FIG. 1 is a schematic diagram of imaging devices of the prior art wherein

FIG. 2 schematically illustrates a frame according to the invention comprising a first portion (FIG. 2a) and a second portion (FIG. 2c) for enclosing a sample (FIG. 2b) within as shown in FIG. 2d;

FIG. 3 schematically depicts a different embodiment of a frame according to the invention comprising a first portion (FIG. 3a) and a second portion (FIG. 3c) for enclosing a sample within a cassette (FIG. 3b) as shown in FIG. 3d;

FIG. 6 schematically illustrates a different embodiment of the invention wherein a sample is enclosed within a frame (FIG. 6a), the frame is positioned in an imaging device (FIGS. 6b and 6c) and the lid of the device is closed (FIG. 6d) prior to imaging the sample.

DETAILED DESCRIPTION OF THE INVENTION

Imaging devices are well known in the art. FIG. 1 depicts a conventional imaging device (10) comprising a housing (14) for a detector (12) which is sensitive to electromagnetic radiation, and a support (16), which is transparent to said electromagnetic radiation, for bearing a sample (20) on its surface. The support (16) is typically made from glass. The sample (20) may take many forms, such as for example, a membrane, tissue slice or section, slide, microtitre or micro plate or a gel. In FIG. 1, the sample is a gel which has been used to separate proteins by electrophoresis into a number of bands (25) which are to be imaged on the imaging device (10). The detector (12) measures electromagnetic radiation emanating from the sample (20) and is capable of imaging the entire area directly from a fixed position or by scanning the surface of the sample (20) as in a scanning device. The detector (12) can take many forms, fluorescence/phosphorescence and storage phosphor imaging detectors being widely used in the art. Photomultiplier tubes (PMT) and charge coupled devices (CCD) are examples of conventional detectors. The housing (14) of the imaging device (10) typically has a light proof lid (not shown in FIG. 1) which is openable to allow placement of a sample (20) on the support (16) and closable to prevent entry of electromagnetic radiation from external sources.

Figure 1A:
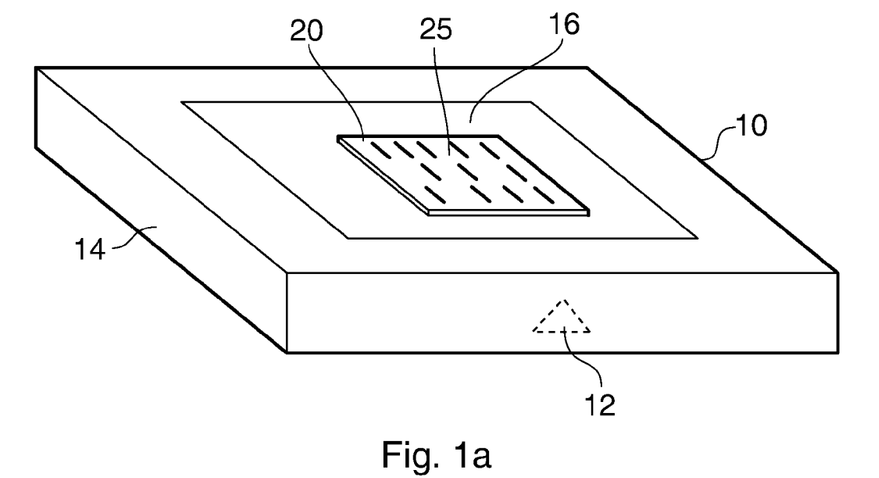
FIG. 1a depicts a naked gel to be imaged supported on a glass sheet of the device, and FIG. 1b a similar gel sandwiched within a cassette supported on the glass sheet.
Figure 1B:
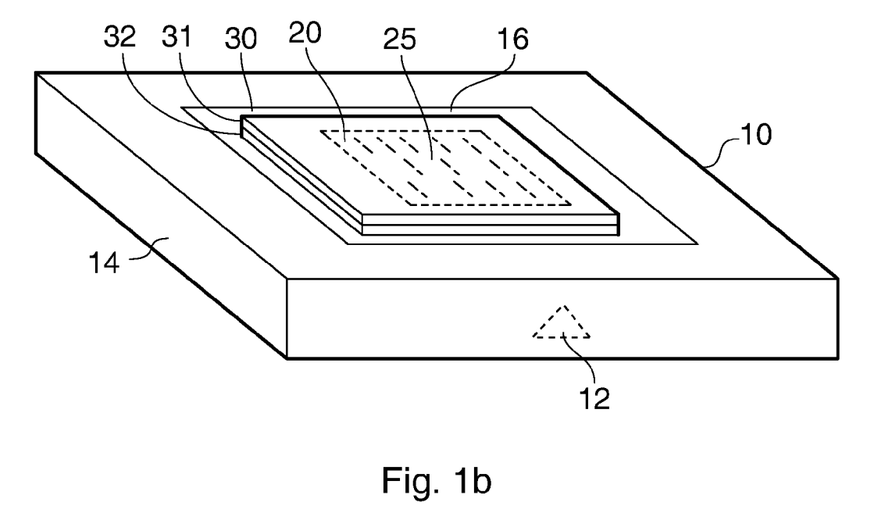

In FIG. 1a the sample (20) is in the form of a naked gel which is placed directly on the support (16) to be imaged. In FIG. 1b the sample (20) is encased or sandwiched within a cassette (30), comprising two glass plates (31, 32), which is positioned on the surface of the support (16). Problems may arise in both situations: in FIG. 1a the support (16) requires extensive cleaning with potentially toxic and/or corrosive chemicals to eliminate all traces of the gel prior to imaging of the next sample while in FIG. 1b interference may occur due to the production of Newton's Rings when light passes through the glass sheets (31, 32) of the cassette (30) and the support (16).

FIG. 2 illustrates the process by which a sample (120) is prepared for imaging by enclosure within a frame (160) of the invention. The frame comprises a first portion (140) and a second portion (150) which are shown in isolation in FIGS. 2a and 2c, respectively. FIG. 2b shows a sample (120) which is subsequently enclosed within the first and second portions (140 & 150) of the frame (160) in readiness for imaging, as shown in FIG. 2d.

Figure 2A:
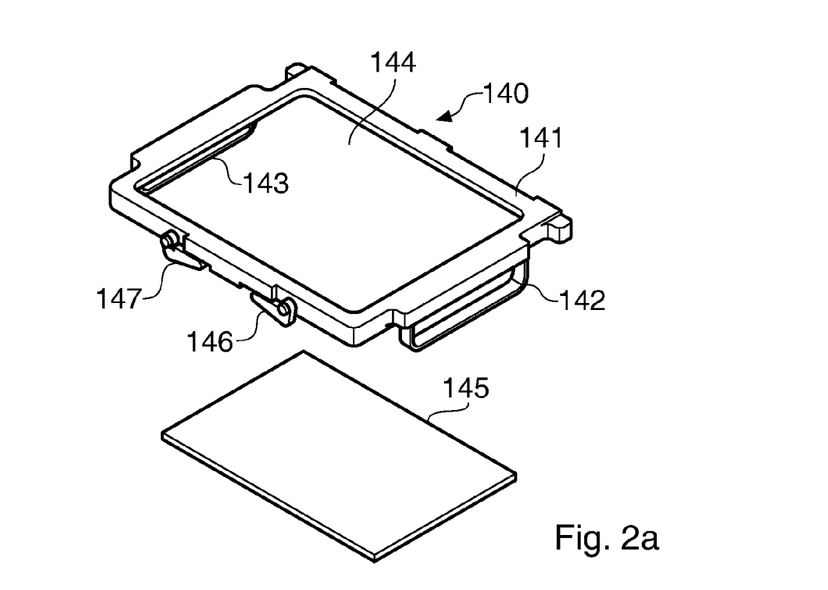

The component parts of the first portion (140) of the frame (160) are depicted in FIG. 2a. The first portion (140) comprises a rectangular body (141) delimiting a window (144) which is transparent to imaging electromagnetic radiation. The rectangular body comprises four connecting walls which are not joined at their upper or lower ends and thus form an open structure. A low fluorescent glass pane (145) is positioned to extend across the entire area of the window (144) in order to support a sample (120) on its surface. It will be understood that the pane (145) may be formed from any material which is transparent to electromagnetic radiation (such as an organic polymer plastic). The glass pane may have reference points (not shown) printed on its surface to facilitate the determination of x and y co-ordinates during image analysis. Handles (142 & 143) are attached to the body (141) to allow carriage of the first portion (140) and/or of the frame (160) when the first portion (140) is connected to the second portion (150). Locks (146 & 147) are provided on the body (141) for securing the first portion (140) to the second portion (160).

Figure 2B:
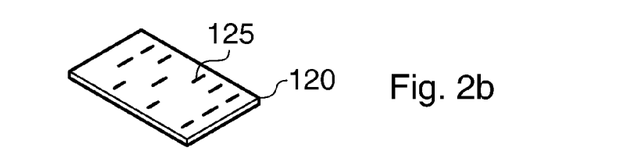
Figure 2C:
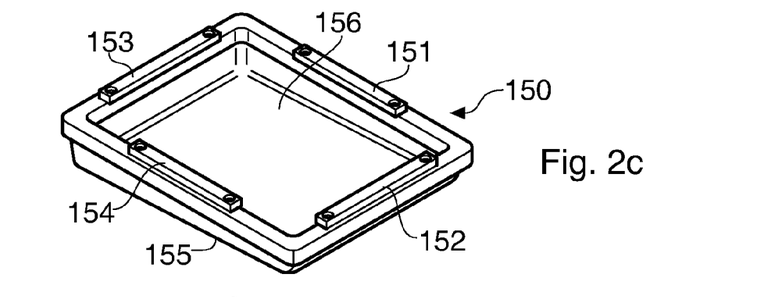

In FIG. 2c the second portion (150) of the frame (160) is shown to comprise a body (155), made of a low fluorescence material, shaped in the form of a light-tight lid (which is opaque to imaging electromagnetic radiation) for the first portion. Spring loaded glass holders (151-154) are attached to one surface of the lid which can be used to secure a cassette (see FIG. 3) to the second portion (150). The centre (156) of the second portion (150) is hollowed such that the body (155) has a concave structure.

A sample (120), exemplified in the diagram by an electrophoresis gel which has been used to separate proteins into distinct bands (e.g. 125), is shown in FIG. 2b.

Figure 2D:
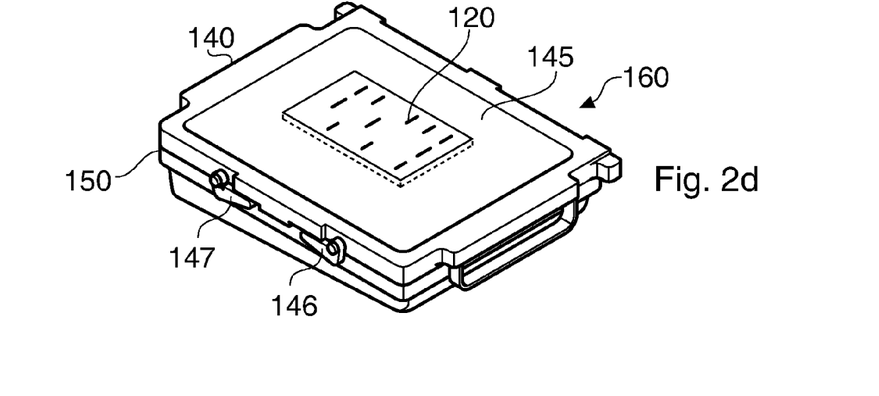

FIG. 2d illustrates the frame (160) containing a sample (120) in readiness for imaging. The sample (120) is placed upon the glass pane (145) of the first portion (140) which is then secured to the second portion (150) by means of the locks (146 & 147). The sample (120) is thus enclosed within the first portion (140) and the second portion (150) of the frame (160) in readiness for imaging. It will be understood by the person skilled in the art that the orientation of the frame (160) shown in FIG. 2d is for illustrative purposes only and that the frame (160) would normally be inverted through 180° prior to insertion into an imaging device for imaging.

FIG. 3 depicts a similar process to that of FIG. 2 whereby a frame (260) of the invention encloses a sample (220) in preparation for imaging; in contrast to the process of FIG. 2 wherein the sample (120) is enclosed directly within the frame (160), in FIG. 3 the sample (220) is already sandwiched within a cassette (230) prior to enclosing the cassette within the frame (260).

Figure 3A:
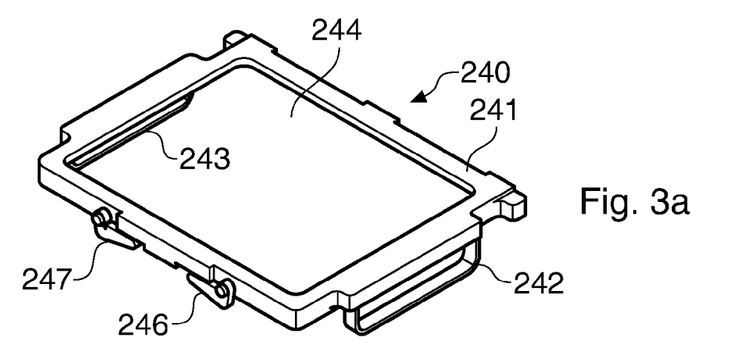

FIG. 3a shows a first portion (240) of the frame (260) of the invention. The first portion (240) comprises a rectangular body (241) which defines a window (244) which is transparent to electromagnetic radiation. The rectangular body (241) comprises four connecting walls which are not joined at their upper or lower ends and thus form an open structure. Handles (242 & 243) are provided to facilitate transport of the first portion (240) and the frame (260), while locks (246 & 247) enable secure connection of the first (240) to the second (250) portion.

Figure 3B:
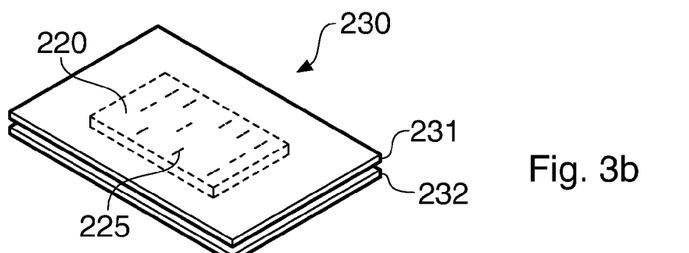

A sample (220), in the form of an electrophoretic gel which has been used for protein separation into discrete bands (225), enclosed within a glass cassette (230) which comprises two glass sheets (231 & 232), is shown in FIG. 3b.

Figure 3C:
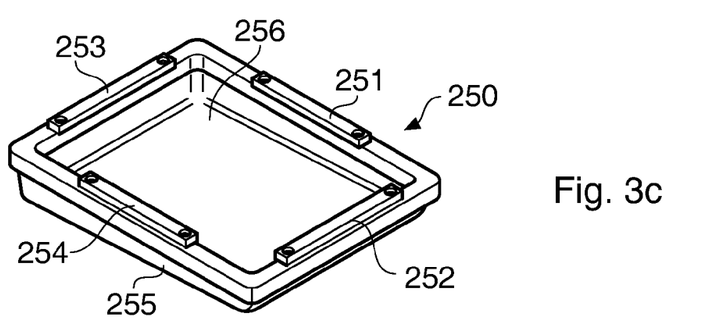

The cassette (230) is attached to the second portion (250) as shown in FIG. 3c. The second portion (250) is identical to that described in FIG. 2b and comprises a body (255), made of a low fluorescence material, shaped in the form of a light-tight lid for the first portion (240). Spring loaded glass holders (251-254) are attached to one surface of the lid for securing the cassette (230) to the second portion (250). These resilient holders (251-254) can be raised by force to allow insertion of the cassette (230) below and then lowered to affix the cassette (230) to the body (255) of the second portion (250).

Figure 3D:
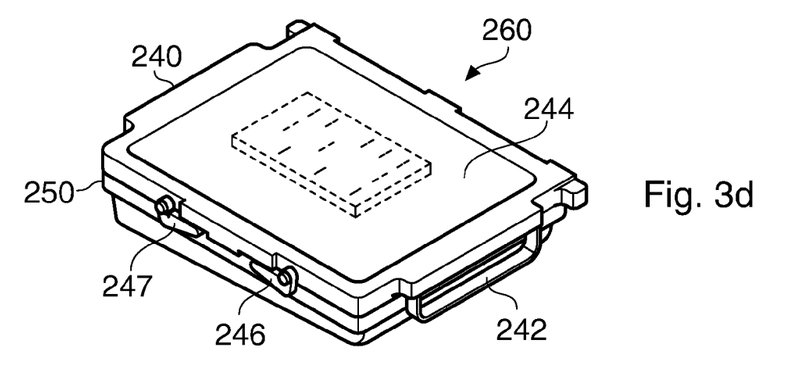

In FIG. 3d the cassette (230, not shown) is enclosed within the frame (260) (which comprises the first (240) and second (250) portions) in readiness for imaging. The frame (260) is as described in FIG. 2d except that it lacks the glass pane (145). As will be understood by the person skilled in the art, the frame (260) is normally inverted through 180° prior to transferring to an imaging device in readiness for imaging.

Figure 4:
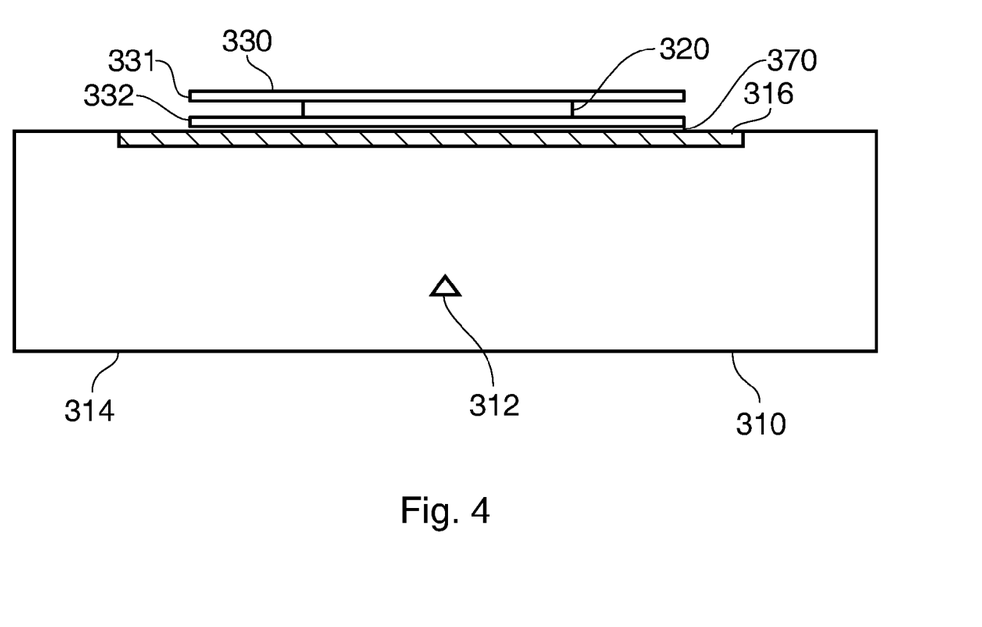
FIG. 4 illustrates the problem of 'Newton's Rings' which can arise with prior art imaging devices.

FIG. 4 illustrates the problem of interference caused by Newton's Rings. The cross-sectional diagram shows an imaging device (310) comprising a detector (312) for measuring electromagnetic radiation having a glass support (316) on which is placed a sample (320) sandwiched within a cassette (330). The cassette consists of two glass plates (331 & 332) which enclose the sample (an electrophoretic gel in the example shown). Newton's Rings (not shown) appear when an air gap (370) between the glass plate (332) of the cassette (330) and the glass support (316) is of a certain size relative to the wavelength of electromagnetic radiation and cause interference in the radiation received by the detector (312).

Figure 5:
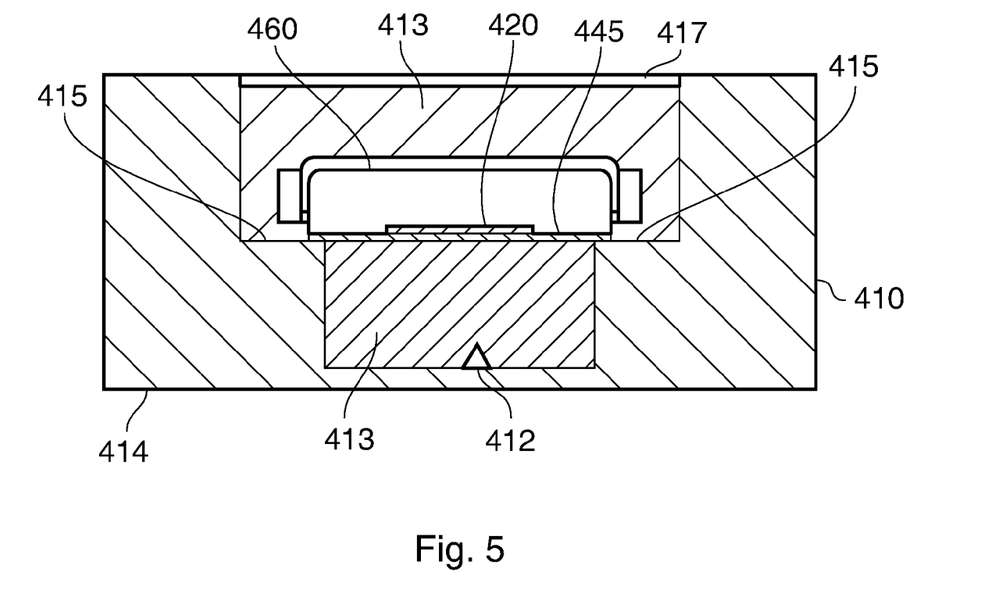
FIG. 5 is a schematic representation in transverse section of a frame according to the invention positioned within an imaging device according to the invention.

FIG. 5, in transverse section, is a schematic diagram of an imaging device (410), according to the invention, imaging a sample (420) enclosed within a frame (460) according to the invention. The imaging device (410) comprises a body (414) enclosing a detector (412) within a chamber (413) which has a pane free platform (415), having an opening (defined in the diagram by the chamber (413)), for supporting a frame (460).

For the purposes of illustration, the frame (460) is the same as that described in FIG. 2 but it will be understood that the frame (260) of FIG. 3 could equally well be used in the imaging device (410). The frame (460) is positioned on the platform (415) within the chamber (413) of the imaging device (410) and the chamber (413) sealed by closure of the lid (417) to prevent entry of external light. A sample (420), in the form of an electrophoretic gel, rests upon a glass pane (445) within the frame (460). The frame (460) is positioned on the platform (415) such that the pane (445) faces the detector (412) and there is an opening (defined by the chamber (413)) between the pane (413) and the detector (412). It will be understood that the purpose of the pane free platform (415) is to avoid the problem of interference caused by Newton's Rings and to eliminate the need for pane cleaning experienced with prior art imaging devices.

Electromagnetic radiation emitted from the sample (420) is detected by the detector (412). In the example shown, the sample is moved across the path of the detector (412) to facilitate scanning of the gel. It will be understood that in another embodiment the detector (412) could be movable in order to scan the surface of the gel. The detector (412) in FIG. 5 is a fluorescence detector and the imaging device irradiates the gel (420) with electromagnetic radiation at a frequency selected to excite fluorophores present within the gel prior to detecting the fluorescence subsequently emitted from the gel (420).

A different embodiment of an imaging device (510) and frame (560) according to the invention is shown in FIG. 6. The figure depicts the process by which a sample (520) is enclosed within a frame (560) and positioned within an imaging device (510) in readiness for imaging.

Figure 6A:
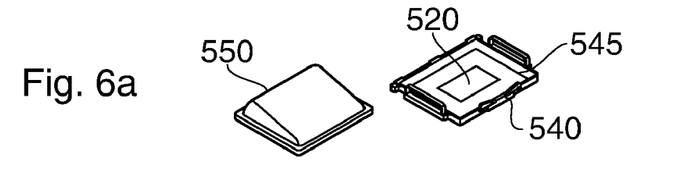

In FIG. 6a a sample (520), in the form of an electrophoretic gel, has been placed on a glass pane (545) in a first portion (540) of a frame (560). The second portion (550) is then connected to the first portion (540) to produce a frame (560) according to the invention.

Figure 6B:
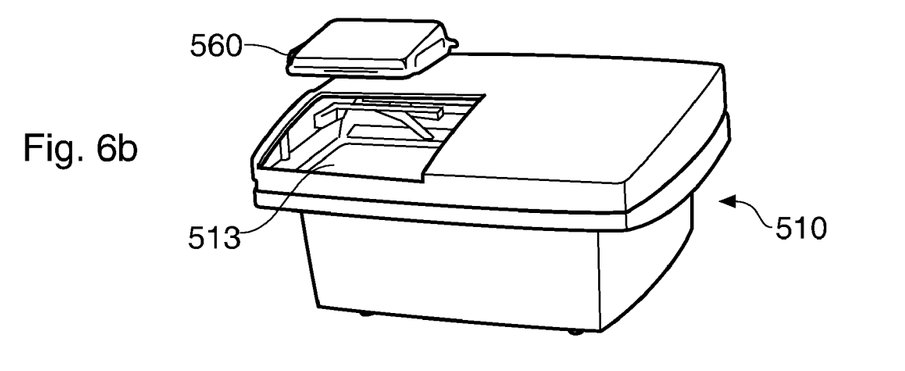

FIG. 6b schematically illustrates the frame (560) in position above the chamber (513) of the imaging device (510). The chamber (510) defines a platform which has an opening for supporting the frame.

Figure 6C:
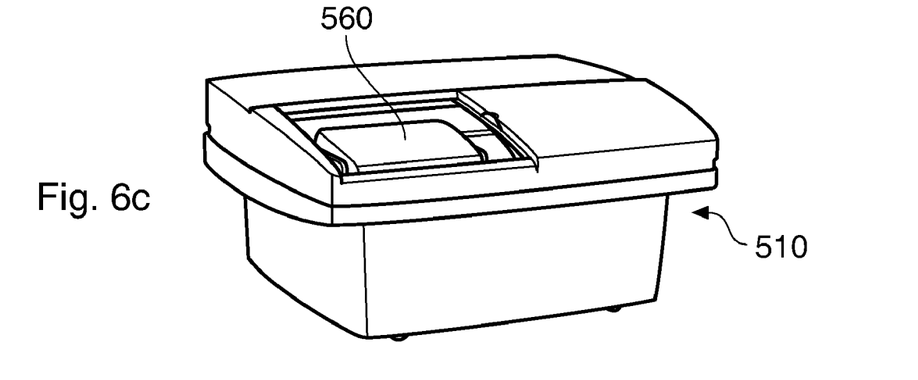

The frame (560) is shown following insertion into the imaging device (510) in FIG. 6c.

Figure 6D:
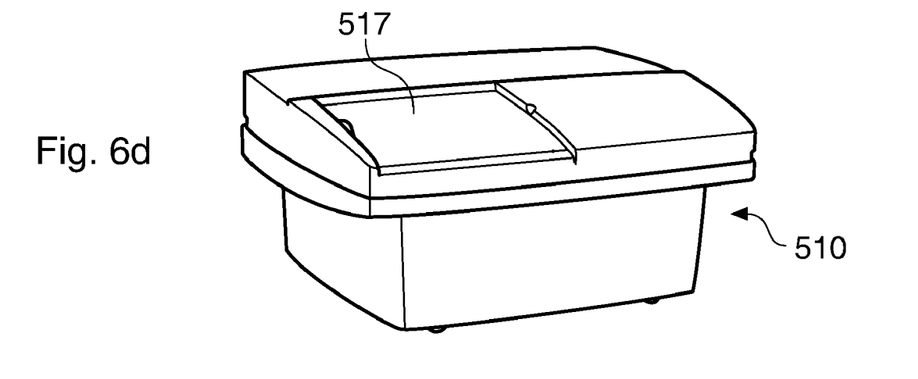

On closure of the light proof lid (517) the sample (520) is ready for imaging in the device (510).

It will be understood that the example used for a sample above, i.e. a gel, was merely for illustrative purposes and that other examples of samples could be used, such as membranes, tissue slices or sections, liquids, microtitre or multi-well plates, cuvettes, tubes, microscope slides or cassettes.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A method for imaging an electrophoresis gel sample comprising the following steps:
   (i) enclosing said electrophoresis gel sample in a frame, said frame comprising a first portion and a second portion providing an hermetic seal between the first portion and said second portion, wherein said first portion comprises a window which is transparent to imaging electromagnetic radiation;
   (ii) positioning the frame in an imaging device, said imaging device comprising an electromagnetic radiation detector and a platform having a pane free opening for supporting the frame, with said window facing said detector and said opening between the window and the detector;
   (iii) irradiating the electrophoresis gel sample with electromagnetic radiation; and
   (iv) capturing electromagnetic radiation emanating from the electrophoresis gel sample with the detector, to form an image of the electrophoresis gel sample.

2. The method of claim 1, wherein said irradiating radiation is scanned across the sample.

3. The method of claim 1, wherein the imaging device is selected from the group consisting of fluorescence/ phosphorescence imager, storage phosphor imager and chemiluminescence imager.

4. The method of claim 1, wherein the detector is a fluorescence detector.

5. The method of claim 1, wherein the detector is a charge coupled device (CCD).

6. The method of claim 1, wherein the detector is a photomultiplier tube (PMT).

7. The method of claim 1, wherein the window lacks a pane.

8. The method of claim 1, wherein the electrophoresis gel sample is held within a cassette and said cassette is enclosed within the frame.

9. The method of claim 1, wherein the frame and the detector are movable relative to each other in order to allow capture of electromagnetic radiation and/or scanning of the sample surface.

10. An imaging device for imaging an electrophoresis gel sample enclosed within a frame, said frame comprising a first portion and a second portion wherein said first portion comprises a body delimiting a window which is transparent to imaging electromagnetic radiation and said second portion is in the form of a lid which is opaque to imaging electromagnetic radiation, the frame enclosing said electrophoresis gel sample, and a platform which has a pane free opening for supporting the frame.

11. The imaging device of claim 10, further comprising a staging mechanism for movement of the frame to enable scanning of the electrophoresis gel sample.

12. The imaging device of claim 11, wherein said imaging device is selected from the group consisting of storage phosphor imager, chemiluminescence scanner, and fluorescence/ phosphorescence scanner.

* * * * *